United States Patent
Ferrari et al.

(10) Patent No.: US 10,993,892 B2
(45) Date of Patent: *May 4, 2021

(54) ANHYDROUS COMPOSITION IN AEROSOL FORM COMPRISING AN ANTIPERSPIRANT ACTIVE AGENT AND A WATER-INSOLUBLE FILM-FORMING BLOCK ETHYLENIC POLYMER AND A PHENYL SILICONE

(71) Applicant: L'OREAL, Paris (FR)

(72) Inventors: Veronique Ferrari, Maisons-Alfort (FR); Laure Ramos-Stanbury, Antony (FR); Xavier Jalenques, Gennevilliers (FR)

(73) Assignee: L'OREAL, Paris (FR)

( * ) Notice: Subject to any disclaimer, the term of this patent is extended or adjusted under 35 U.S.C. 154(b) by 146 days.

This patent is subject to a terminal disclaimer.

(21) Appl. No.: 15/533,539

(22) PCT Filed: Dec. 10, 2015

(86) PCT No.: PCT/EP2015/079329
§ 371 (c)(1),
(2) Date: Jun. 6, 2017

(87) PCT Pub. No.: WO2016/092052
PCT Pub. Date: Jun. 16, 2016

(65) Prior Publication Data
US 2017/0360658 A1    Dec. 21, 2017

(30) Foreign Application Priority Data
Dec. 10, 2014   (FR) ...................................... 1462198

(51) Int. Cl.
| | | |
|---|---|---|
| *A61K 8/04* | (2006.01) | |
| *A61K 8/26* | (2006.01) | |
| *A61K 8/28* | (2006.01) | |
| *A61Q 15/00* | (2006.01) | |
| *A61K 8/90* | (2006.01) | |
| *A61K 8/891* | (2006.01) | |
| *A61K 8/89* | (2006.01) | |

(52) U.S. Cl.
CPC ................ *A61K 8/046* (2013.01); *A61K 8/26* (2013.01); *A61K 8/28* (2013.01); *A61K 8/89* (2013.01); *A61K 8/891* (2013.01); *A61K 8/90* (2013.01); *A61Q 15/00* (2013.01); *A61K 2800/31* (2013.01)

(58) Field of Classification Search
CPC . A61K 8/046; A61K 8/89; A61K 8/26; A61K 8/891; A61K 8/28; A61K 8/90; A61K 2800/31; A61Q 15/00
See application file for complete search history.

(56) References Cited

U.S. PATENT DOCUMENTS

| | | | |
|---|---|---|---|
| 6,403,070 B1 * | 6/2002 | Pataut .................. | A61K 8/0279 424/400 |
| 2012/0003284 A1 * | 1/2012 | Arnaud ................ | A61K 8/0229 424/401 |

FOREIGN PATENT DOCUMENTS

| | | |
|---|---|---|
| EP | 1 103 249 A1 | 5/2001 |
| FR | 2 990 854 A1 | 11/2013 |
| WO | WO-91/18587 A1 | 12/1991 |
| WO | WO-98/13014 A1 | 4/1998 |
| WO | WO-2014/048648 A1 | 4/2014 |

\* cited by examiner

*Primary Examiner* — Matthew P Coughlin
*Assistant Examiner* — Thurman Wheeler
(74) *Attorney, Agent, or Firm* — Polsinelli PC

(57) ABSTRACT

The present invention relates to an anhydrous composition in aerosol form comprising, in particular in a physiologically acceptable medium:
a) an oily phase comprising
   i) at least one volatile oil, and
   ii) at least one nonvolatile hydrocarbon-based oil, and
   iii) at least one phenyl silicone, and
b) at least one antiperspirant active agent chosen from aluminum and/or zirconium salts or complexes,
c) at least one water-insoluble film-forming block ethylenic polymer
d) at least one propellant.
The invention also relates to a cosmetic process for treating human perspiration, and optionally the body odors associated with human perspiration, especially underarm odors, comprising the application of said composition to a surface of the skin.

23 Claims, No Drawings

ANHYDROUS COMPOSITION IN AEROSOL FORM COMPRISING AN ANTIPERSPIRANT ACTIVE AGENT AND A WATER-INSOLUBLE FILM-FORMING BLOCK ETHYLENIC POLYMER AND A PHENYL SILICONE

CROSS REFERENCE TO RELATED APPLICATIONS

This application is a National Phase filing under 35 U.S.C. § 371 of PCT/EP2015/079329 filed on Dec. 10, 2015; and this application claims priority to Application No. 1462198 filed in France on Dec. 10, 2014 under 35 U.S.C. § 119. The entire contents of each application are hereby incorporated by reference.

The present invention relates to an anhydrous composition in aerosol form comprising, in particular in a physiologically acceptable medium:
a) an oily phase comprising
i) at least one volatile oil, and
ii) at least one nonvolatile hydrocarbon-based oil, and
iii) at least one phenyl silicone, and
b) at least one antiperspirant active agent chosen from aluminum and/or zirconium salts or complexes,
c) at least one water-insoluble film-forming block ethylenic polymer,
d) at least one propellant.

The invention also relates to a cosmetic process for treating human perspiration, and optionally the body odors associated with human perspiration, especially underarm odors, comprising the application of said composition to a surface of the skin.

The present invention also relates to the use of said cosmetic composition and also to an aerosol device using it.

The armpits and also certain other parts of the body are generally the site of much discomfort that may arise directly or indirectly from perspiration. This perspiration often leads to unpleasant and disagreeable sensations that are mainly due to the presence of sweat resulting from perspiration, which may, in certain cases, make the skin and clothing wet, especially in the region of the armpits or of the back, thus leaving visible marks. Finally, during its evaporation, sweat may also leave salts and/or proteins on the surface of the skin, which thus results in whitish marks on clothing. Such discomfort is noticed, including in the case of moderate perspiration.

In the cosmetic field, it is thus well known to use, in topical application, antiperspirant products containing substances that have the effect of limiting or even preventing the flow of sweat in order to overcome the problems mentioned above. These products are generally available in the form of roll-ons, sticks, aerosols or sprays.

Antiperspirant substances are generally constituted of aluminum and/or zirconium salts or complexes, such as aluminum chloride and aluminum hydroxyhalides. These substances make it possible to reduce the flow of sweat.

However, some cosmetic compounds based on these antiperspirant substances can lead to a tacky effect which is uncomfortable for the consumer. Some in addition have a tendency to transfer onto clothing, leaving unsightly visible marks.

In order to overcome the problem of marks, antiperspirant compositions containing oils with a refractive index close to those of aluminum salts have been developed. The role of such oils is to reduce the whitish appearance of antiperspirant compositions when they are deposited on the skin and, consequently, to make the marks on clothing less white. The oils used are generally fatty acid esters such as isopropyl myristate or polydimethylsiloxanes. Such compositions have been particularly described in patents or patent applications EP 1362885, JP 03095111 and FR 2242969.

However, such antiperspirant compositions have the drawback of giving the skin, especially on the armpits, an oily sensation that the user finds unpleasant, and do not make it possible to limit the transfer of antiperspirant products from the skin onto clothing. There is thus a real need to use antiperspirant cosmetic compositions in aerosol form, which do not have the drawbacks mentioned above, i.e. compositions which make it possible to substantially reduce the tacky effect while at the same time maintaining good antiperspirant efficacy and which make it possible to achieve less transfer onto fabrics.

The applicant has therefore discovered, surprisingly, that, by applying to the skin an anhydrous composition in aerosol form comprising, in particular in a physiologically acceptable medium:
a) an oily phase comprising
i) at least one volatile oil, and
ii) at least one nonvolatile hydrocarbon-based oil, and
iii) at least one phenyl silicone, and
b) at least one antiperspirant active agent chosen from aluminum and/or zirconium salts or complexes, and
c) at least one water-insoluble film-forming block ethylenic polymer defined hereinafter, and
d) at least one propellant, it is possible to minimize the problems of tackiness of the antiperspirant compositions on fabrics while at the same time maintaining an antiperspirant efficacy.

Thus, the antiperspirant cosmetic composition in aerosol form in accordance with the invention makes it possible to reduce the tackiness and to maintain good antiperspirant efficacy. It also makes it possible to be able to produce formulas which transfer less onto textiles, thereby generating fewer unsightly visible marks on clothing, in particular on dark-colored clothing, in comparison with a standard antiperspirant composition or an antiperspirant composition containing oils.

In particular, the antiperspirant cosmetic composition makes it possible to significantly reduce the whitish marks on clothing, in particular on dark-colored clothing.

Moreover, the antiperspirant cosmetic composition in aerosol form in accordance with the invention can lead to formulas which transfer less onto textiles, thus giving rise to fewer unsightly visible marks on clothing, especially on dark-colored clothing, when compared with a standard antiperspirant composition or an antiperspirant composition containing oils.

Thus, the use of the water-insoluble block ethylenic polymers as described below in an antiperspirant composition based on aluminum salts makes it possible to reduce the transfer of unsightly visible marks onto clothing without harming the efficacy of the aluminum salts. Furthermore, the water-insoluble block ethylenic polymers used prove to be compatible with the aluminum salts since they do not form a macroscopically visible precipitate in the composition.

The use of a phenyl silicone in the composition in accordance with the invention makes it possible to reduce the tackiness after application to the keratin material A subject of the present invention is therefore in particular an anhydrous composition in aerosol form comprising, in particular in a physiologically acceptable medium:
a) an oily phase comprising
i) at least one volatile oil, and
ii) at least one nonvolatile hydrocarbon-based oil, and
iii) at least one phenyl silicone, and b) at least one antiperspirant active agent chosen from aluminum and/or zirconium salts or complexes, c) at least one water-insoluble film-forming block ethylenic polymer comprising a first block with a glass transition temperature (Tg) of greater than or equal to 85° C. and a second block with a Tg of less than or equal to 20° C., and d) at least one propellant.

The cosmetic composition according to the invention has both good transfer-resistance and antiperspirant properties.

Moreover, the present invention also relates to a cosmetic process for treating human perspiration, and optionally the body odors associated with human perspiration, which consists in applying to the surface of a human keratin material an effective amount of the cosmetic composition as described previously.

The process according to the invention is particularly advantageous for treating armpit perspiration, since the composition used does not give an unpleasant oily sensation and transfers less onto clothing, while at the same time efficiently treating perspiration.

The invention also relates to the use of said composition for cosmetically treating human perspiration.

Other subjects, characteristics, aspects and advantages of the invention will emerge even more clearly on reading the description and the examples that follow.

For the purposes of the present invention, the term "physiologically acceptable medium" is intended to denote a medium that is suitable for the topical administration of a composition, i.e. a medium which is colorless and has no unpleasant appearance, and which is perfectly compatible with the topical route of administration. In the present case, where the composition is intended for topical administration, i.e. by application at the surface of the keratin material under consideration, such a medium is considered in particular to be physiologically acceptable when it does not cause stinging, tautness or redness that is unacceptable to the user.

For the purposes of the present invention, the term "anhydrous" is intended to mean a liquid phase with a water content of less than 5% by weight, preferably less than 2% by weight and even more preferably less than 1% by weight relative to the weight of said composition. It should be noted that the water in question is more particularly bound water, such as the water of crystallization in salts, or traces of water absorbed by the raw materials used in the production of the compositions according to the invention.

The term "human keratin materials" is intended to mean the skin (of the body, face and around the eyes), hair, eyelashes, eyebrows, bodily hair, nails, lips or mucous membranes.

The term "final composition" is intended to mean the combination of the liquid phase and of the propellant gas.

Antiperspirant Active Agent

The term "antiperspirant" is intended to mean a salt which, by itself, has the effect of reducing the flow of sweat, of reducing the sensation on the skin of moisture associated with human sweat and of masking human sweat.

As indicated previously, the cosmetic composition comprises one or more antiperspirant active agents chosen from aluminum and/or zirconium salts or complexes.

Among the aluminum salts or complexes, mention may be made of aluminum halohydrates.

Among the aluminum salts, mention may in particular be made of aluminum chlorohydrate, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the Aluminum sesquichlorohydrex-propylene glycol complex, aluminum sulfate buffered with sodium aluminum lactate.

Aluminum sesquichlorohydrate is in particular sold under the trade name Reach 301® by the company Summitreheis.

Aluminum chlorohydrate is in particular sold under the trade names Locron S FLA®, Locron P and Locron L.ZA by the company Clariant; under the trade names Microdry Aluminum Chlorohydrate®, Micro-Dry 323®, Chlorhydrol 50, Reach 103 and Reach 501 by the company Summitreheis; under the trade name Westchlor 200® by the company Westwood; under the trade name Aloxicoll PF 40® by the company Guilini Chemie; Cluron 50%® by the company Industria Quimica Del Centro; or Clorohidroxido Aluminio SO A 50%® by the company Finquimica.

Aluminum chlorohydrate, aluminum sesquichlorohydrate and mixtures thereof will more particularly be used.

The aluminum salts or complexes may be present in the final composition according to the invention in a content ranging from 1% to 25% by weight, preferably in a content ranging from 2% to 20% and more particularly between 3% and 15% by weight relative to the total weight of the final composition.

Ethylenic Polymer

As indicated previously, the cosmetic composition comprises one or more water-insoluble film-forming block ethylenic polymers comprising a first block with a glass transition temperature (Tg) of greater than or equal to 85° C. and a second block with a Tg of less than or equal to 20° C.

The term "ethylenic polymer" is intended to mean a polymer obtained by polymerization of monomers comprising one or more ethylenic unsaturations.

The term "film-forming polymer" is intended to mean a polymer that is capable of forming, by itself or in the presence of an auxiliary film-forming agent, a continuous film that adheres to a support, especially to keratin materials such as the skin, the hair, the eyelashes or the nails, especially the skin.

The term "water-insoluble polymer" is intended to mean that the polymer is not soluble, according to the definition below.

The term "soluble polymer" is intended to mean that the polymer dissolves in water or in a 50/50 by volume mixture of water and ethanol, or alternatively a mixture of water and isopropanol, without modification of the pH, at a solids content of 5% by weight, at ambient temperature (25° C., 1 atm.). The polymer is considered to be soluble if it does not form a precipitate or agglomerate that is visible to the naked eye when it is placed in solution, and if it therefore gives a clear solution.

Preferably, the polymer according to the invention is a polymer of linear or grafted structure. In contrast, a polymer of non-linear or ungrafted structure is, for example, a polymer of star or crosslinked structure.

The block ethylenic polymer according to the invention is preferentially prepared exclusively from monofunctional monomers. This means that the block ethylenic polymer does not contain any multifunctional monomers, which make it possible to break the linearity of a polymer so as to obtain in particular a crosslinked polymer, as a function of the content of multifunctional monomer.

Preferably, the polymer according to the invention is a non-elastomeric polymer, i.e. a polymer which, when it is subjected to a stress intended to stretch it (for example by 30% relative to its initial length), does not return to a length substantially identical to its initial length when the stress ceases.

More specifically, the term "non-elastomeric polymer" denotes a polymer with an instantaneous recovery Ri<50% and a delayed recovery $R_{2h}$<70% after having been subjected to a 30% elongation. Preferably, Ri is <30% and $R_{2h}$ is <50%.

The non-elastomeric nature of the polymer may be determined according to the following protocol: A polymer film is prepared by pouring a solution of the polymer in a Teflon-coated mould, followed by drying for 7 days in an environment conditioned at 23±5° C. and 50±10% relative humidity. A film about 100 μm thick is then obtained, from which are cut rectangular specimens (for example using a sample punch) 15 mm wide and 80 mm long. These specimen-shaped samples are subjected to a tensile stress using a machine sold under the reference Zwick, under the same temperature and humidity conditions as for the drying.

The specimens are stretched at a speed of 50 mm/min and the distance between the jaws is 50 mm, which corresponds to the initial length (l0) of the specimen.

The instantaneous recovery Ri is determined in the following manner:
- the specimen is stretched by 30% (εmax), i.e. approximately 0.3 times its initial length (l0);
- the stress is removed by imposing a return speed equal to the tensile speed, i.e. 50 mm/minute, and the residual elongation of the specimen is measured as a percentage, after returning to zero stress (εi).

The instantaneous recovery Ri (as a percentage) is given by the formula below:

$$Ri = ((\epsilon max - \epsilon i)/\epsilon max) \times 100$$

To determine the delayed recovery, the percentage residual elongation of the specimen (ε2h) is measured two hours after returning to zero stress. The delayed recovery $R_{2h}$ (as a percentage) is given by the following formula:

$$R_{2h} = ((\epsilon max - \epsilon 2h)/\epsilon max) \times 100$$

The polymer according to the present invention is a block polymer, comprising a first block with a Tg of greater than or equal to 85° C. and a second block with a Tg of less than or equal to 20° C.

It is pointed out that the terms "first" and "second" blocks do not in any way condition the order of said blocks in the structure of the polymer.

Preferably, the polymer comprises two distinct blocks (diblock) or, preferentially, three distinct blocks (triblocks).

Preferably, said first and second blocks are mutually incompatible. The term "mutually incompatible blocks" is intended to mean that the mixture formed from the polymer corresponding to the first block and from the polymer corresponding to the second block is not miscible in the polymerization solvent that is in major amount by weight of the block polymer, at ambient temperature (25° C.) and atmospheric pressure ($10^5$ Pa), for a content of the polymer mixture of greater than or equal to 5% by weight, relative to the total weight of the mixture (polymers and solvent), it being understood that:
i) said polymers are present in the mixture in a content such that the respective weight ratio ranges from 10/90 to 90/10, and that
ii) each of the polymers corresponding to the first and second blocks has an average (weight-average or number-average) molecular mass equal to that of the block polymer ±15%.

In the case of a mixture of polymerization solvents, and in the event that two or more solvents are present, said polymer mixture is immiscible in at least one of them. Needless to say, in the case of a polymerization performed in a single solvent, this solvent is the solvent that is in major amount.

The glass transition temperatures (Tg) indicated are, unless otherwise indicated, theoretical Tg values determined from the theoretical Tg values of the constituent monomers of each of the blocks, which may be found in a reference manual such as the Polymer Handbook, 4th Edition, (Brandrup, Immergut, Grulke), 1999, John Wiley, according to the following relationship, known as Fox's law:

$$\frac{1}{Tg} = \sum_i \left(\frac{\varpi i}{Tgi}\right)$$

wi being the mass fraction of the monomer i in the block under consideration and Tgi being the glass transition temperature of the homopolymer of the monomer i (expressed in degrees Kelvin).

The polymer according to the invention thus comprises a block with a Tg of greater than or equal to 85° C., for example between 85 and 175° C., preferably between 90 and 150° C. and especially between 100 and 130° C.

The polymer according to the invention also comprises a block with a Tg of less than or equal to 20° C., for example between −100 and 20° C., preferably between −80 and 15° C. and especially between −60 and 10° C.

Preferably, the block with a Tg of greater than or equal to 85° C. represents 50% to 90% by weight and preferably 60% to 80% by weight relative to the weight of the final polymer.

Preferably, the block with a Tg of less than or equal to 20° C. represents 5% to 50% by weight and preferably 10% to 40% by weight relative to the weight of the final polymer.

Preferably, said first and second blocks are linked together via an intermediate segment comprising at least one constituent monomer of said first block and at least one constituent monomer of said second block.

The intermediate segment is preferably a block comprising at least one constituent monomer of the first block and at least one constituent monomer of the second block of the polymer, allowing these blocks to be "compatibilized". Said intermediate segment or block is preferably a random copolymer.

Preferably, said intermediate segment or block is derived essentially from constituent monomers of the first block and of the second block.

The term "essentially" is intended to mean at least 85%, preferably at least 90%, better still 95% and even better still 100%.

Preferably, said block ethylenic polymer has a polydispersity index Ip of greater than 2, especially between 2 and 9, preferably between 2.3 and 8 and better still between 2.4 and 7. The polydispersity index Ip is equal to the ratio of the weight-average molar mass Mw to the number-average molar mass Mn.

The weight-average molar mass (Mw) and number-average molar mass (Mn) are determined by gel permeation liquid chromatography (THF solvent, calibration curve established with linear polystyrene standards, UV and refractometric detector).

The weight-average molar mass (Mw) of the block ethylenic polymer is preferably between 35 000 and 300 000 and better still between 45 000 and 150 000 g/mol.

The number-average molar mass (Mn) of the block ethylenic polymer is preferably between 10 000 and 70 000 and better still between 12 000 and 50 000 g/mol.

Each block of the polymer according to the invention is derived from one type of monomer or from several different types of monomers. This means that each block may be a homopolymer or a copolymer, which may be random, alternating or of another form; preferably random. The chemical nature and/or the amount of the monomers constituting each of the blocks may obviously be chosen by a person skilled in the art, on the basis of his general knowledge, to obtain blocks having the required Tg values.

The block with a Tg of greater than or equal to 85° C., or first block, may thus be a homopolymer or a copolymer. It preferably comprises at least one monomer with a Tg of greater than or equal to 85° C.

When this block is a homopolymer, it may be derived from a monomer such that the homopolymer prepared from this monomer has a Tg of greater than or equal to 85° C.

When this block is a copolymer, it may be derived from one or more monomers whose nature and concentration are chosen such that the Tg of the resulting copolymer is greater than or equal to 85° C. The copolymer may comprise, for example, monomers which are such that the homopolymers prepared from these monomers have Tg values of greater than or equal to 85° C., for example a Tg ranging from 85 to 175° C., alone or as a mixture with monomers which are such that the homopolymers prepared from these monomers have Tg values of less than 85° C., preferably chosen from monomers with a Tg of between −100 and 85° C.

Similarly, the block with a Tg of less than or equal to 20° C., or second block, may be a homopolymer or a copolymer. It preferably comprises at least one monomer with a Tg of less than or equal to 20° C.

When this block is a homopolymer, it may be derived from a monomer such that the homopolymer prepared from this monomer has a Tg of less than or equal to 20° C.

When this block is a copolymer, it may be derived from one or more monomers whose nature and concentration are chosen such that the Tg of the resulting copolymer is less than or equal to 20° C. It may comprise, for example, monomers whose corresponding homopolymer has a Tg of less than or equal to 20° C., for example a Tg ranging from −100° C. to 20° C., alone or as a mixture with monomers whose corresponding homopolymer has a Tg of greater than 20° C., preferably chosen from monomers with a Tg of between 20 and 175° C.

The monomers whose homopolymer has a glass transition temperature (Tg) of greater than or equal to 85° C. (also known as monomers with a Tg of greater than or equal to 85° C.) may be chosen from the following monomers, alone or as a mixture:

the methacrylates of formula $CH_2=C(CH_3)—COOR_1$ in which $R_1$ represents a methyl or tert-butyl group; or a $C_6$ to $C_{12}$ cycloalkyl group such as isobornyl;

the acrylates of formula $CH_2=CH—COOR_2$ in which $R_2$ represents a $C_6$ to $C_{12}$ cycloalkyl group such as isobornyl, or a tert-butyl group;

the (meth)acrylamides of formula $CH_2=C(CH_3)—CONR_7R_8$ or $CH_2=CH—CONR_7R_8$, in which $R_7$ and $R_8$, which may be identical or different, represent a hydrogen atom or a methyl or isopropyl group; or $R_7$ represents H and $R_8$ represents a branched $C_3$ to $C_5$ group such as an isopropyl, sec-butyl, tert-butyl or 1-methylbutyl group; mention may be made of N-t-butylacrylamide, N-isopropylacrylamide and N,N-dimethylacrylamide;

styrene and derivatives thereof such as chlorostyrene.

Most particularly, mention may be made of methyl methacrylate, tert-butyl (meth)acrylate and isobornyl (meth)acrylate, and mixtures thereof.

The monomers whose homopolymer has a Tg of less than or equal to 20° C. may be chosen from the following monomers, alone or as a mixture:

the acrylates of formula $CH_2=CHCOOR_3$, with $R_3$ representing a linear or branched $C_1$ to $C_{12}$ alkyl group, with the exception of the tert-butyl group, in which one or more heteroatoms chosen from O, N and S are optionally intercalated, said alkyl group also possibly being substituted with one or more substituents chosen from hydroxyl groups and halogen atoms (Cl, Br, I and F);

the methacrylates of formula $CH_2=C(CH_3)—COOR_4$, with $R_4$ representing a linear or branched $C_6$ to $C_{12}$ alkyl group in which one or more heteroatoms chosen from O, N and S are optionally intercalated, said alkyl group also possibly being substituted with one or more substituents chosen from hydroxyl groups and halogen atoms (Cl, Br, I and F);

the vinyl esters of formula $R_5—CO—O—CH=CH_2$ in which $R_5$ represents a linear or branched $C_4$ to $C_{12}$ alkyl group;

$C_4$ to $C_{12}$ alkyl vinyl ethers, such as butyl vinyl ether and lauryl vinyl ether;

$N—(C_4$-$C_{12}$ alkyl)acrylamides, such as N-octylacrylamide.

Among the monomers with a Tg of less than or equal to 20° C., mention may also be made of the monomers of formula (I) below, alone or as a mixture:

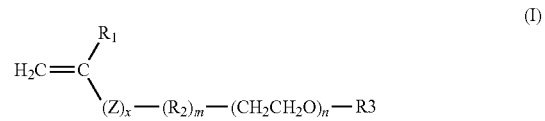

in which:

$R_1$ is a hydrogen atom or a methyl radical;

Z is a divalent group chosen from —COO—, —CONH—, —CONCH_3—, —OCO—, —O—, —SO_2— —CO—O—CO— and —CO—CH_2—CO—;

x is 0 or 1;

$R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si and P;

m is 0 or 1;

n is an integer between 3 and 300 inclusive;

$R_3$ is a hydrogen atom or a linear, branched or cyclic, saturated or unsaturated, optionally aromatic carbon-based radical, of 1 to 30 carbon atoms, which may comprise 1 to 20 heteroatoms chosen from O, N, S, F, Si and P.

Preferably, x=1 and Z represents COO or CONH, preferentially COO.

In the radical $R_2$, the heteroatom(s), when they are present, may be intercalated in the chain of said radical $R_2$, or alternatively said radical $R_2$ may be substituted with one or more groups comprising them such as hydroxyl, amino ($NH_2$, NHR' or NR'R" with R' and R", which may be identical or different, representing a linear or branched $C_1$-$C_{22}$ alkyl, especially methyl or ethyl), —$CF_3$, —CN, —$SO_3H$ or —COOH.

In particular, $R_2$ may comprise a group —O—, —N(R)—, —CO— and a combination thereof, and especially —O—CO—O—, —CO—O—, —N(R)CO—; —O—CO—NR—, —NR—CO—NR—, with R representing H or a linear or branched $C_1$-$C_{22}$ alkyl, optionally comprising 1 to 12 heteroatoms chosen from O, N, S, F, Cl, Br, Si and P.

In particular, $R_2$ may be:
an alkylene radical containing 1 to 20 carbon atoms, such as methylene, ethylene, n-propylene, isopropylene, n-butylene, isobutylene, tert-butylene, pentylene, isopentylene, n-hexylene, isohexylene, heptylene, isoheptylene, n-octylene, isooctylene, nonylene, isononylene, decylene, isodecylene, n-dodecylene, isododecylene, tridecylene, n-tetradecylene, hexadecylene, n-octadecylene, docosanylene or arachinylene;
a substituted or unsubstituted cycloalkylene radical containing 5 to 10 carbon atoms, such as cyclopentylene, cyclohexylene, cycloheptylene, cyclooctylene, cyclononylene or cyclodecylene;
a phenylene radical —$C_6H_4$— (ortho, meta or para), optionally substituted with a $C_1$-$C_{12}$ alkyl radical optionally comprising 1 to 18 heteroatoms chosen from O, N, S, F, Si and P;
a benzylene radical —$C_6H_4$—$CH_2$— optionally substituted with a $C_1$-$C_{12}$ alkyl radical optionally comprising 1 to 18 heteroatoms chosen from O, N, S, F, Si and P;
a radical of formula —$CH_2$—O—CO—O—, —$CH_2$—$CH_2$—O—CO—O—, —$CH_2$—CO—O—, —$CH_2$—$CH_2$—CO—O—, —$CH_2$—O—CO—NH—, —$CH_2$—$CH_2$—O—CO—NH—; —$CH_2$—NH—CO—NH—, —$CH_2$—$CH_2$—NH—CO—NH—; —$CH_2$—CHOH—, —$CH_2$—$CH_2$—CHOH—, —$CH_2$—$CH_2$—CH($NH_2$)—, —$CH_2$—CH($NH_2$)—, —$CH_2$—$CH_2$—CH(NHR')—, —$CH_2$—CH(NHR')—, —$CH_2$—$CH_2$—CH(NR'R'')—, —$CH_2$—CH(NR'R'')—, —$CH_2$—$CH_2$—$CH_2$—NR'—, —$CH_2$—$CH_2$—$CH_2$—O—; —$CH_2$—$CH_2$—CHR'—O— with R' and R'' representing a linear or branched $C_1$-$C_{22}$ alkyl optionally comprising 1 to 12 heteroatoms chosen from O, N, S, F, Si and P;
or a mixture of these radicals.

Preferably, $R_2$ may be:
an alkylene radical containing 1 to 20 carbon atoms, especially methylene, ethylene, n-propylene, n-butylene, n-hexylene, n-octylene, n-dodecylene or n-octadecylene;
a phenylene radical —$C_6H_4$— (ortho, meta or para), optionally substituted with a $C_1$-$C_{12}$ alkyl radical optionally comprising 1 to 18 heteroatoms chosen from O, N, S, F, Si and P; or
a benzylene radical —$C_6H_4$—$CH_2$— optionally substituted with a $C_1$-$C_{12}$ alkyl radical optionally comprising 1 to 18 heteroatoms chosen from O, N, S, F, Si and P.

Preferably, n is between 5 and 200 inclusive, better still between 6 and 120 inclusive, or even between 7 and 50 inclusive.

Preferably, $R_3$ is a hydrogen atom; a phenyl radical optionally substituted with a $C_1$-$C_{12}$ alkyl radical optionally comprising 1 to 20 heteroatoms chosen from O, N, S, F, Si and P; a $C_1$-$C_{30}$, especially $C_1$-$C_{22}$ or even $C_2$-$C_{16}$ alkyl radical, optionally comprising 1 to 18 heteroatoms chosen from O, N, S, F, Si and P; a $C_3$-$C_{12}$, especially $C_4$-$C_8$ or even $C_5$-$C_6$ cycloalkyl radical, optionally comprising 1 to 18 heteroatoms chosen from O, N, S, F, Si and P.

Among the radicals $R_3$, mention may be made of methyl, ethyl, propyl, benzyl, ethylhexyl, lauryl, stearyl and behenyl (—$(CH_2)_{21}$—$CH_3$) chains, and also fluoroalkyl chains, for instance heptadecafluorooctyl sulfonyl amino ethyl $CF_3$—$(CF_2)_7$—$SO_2$—N($C_2H_5$)—$CH_2$—$CH_2$; or alternatively —$CH_2$—$CH_2$—CN, succinimido, maleimido, mesityl, tosyl, triethoxysilane or phthalimide chains.

Preferentially, the monomers of formula (I) are such that:
x=1 and Z represents COO,
m=0,
n=6 to 120 inclusive,
$R_3$ is chosen from a hydrogen atom; a phenyl radical optionally substituted with a $C_1$-$C_{12}$ alkyl radical; a $C_1$-$C_{30}$, especially $C_1$-$C_{22}$ or even $C_2$-$C_{16}$ alkyl radical.

Preferably, the monomers of formula (I) have a molecular weight of between 300 and 5000 g/mol.

Among the monomers of formula (I) that are particularly preferred, mention may be made of:
poly(ethylene glycol) (meth)acrylate in which $R_1$ is H or methyl; Z is COO, x=1, m=0 and $R_3$=H;
methylpoly(ethylene glycol) (meth)acrylate, also known as methoxypoly(ethylene glycol) (meth)acrylate, in which $R_1$ is H or methyl; Z is COO, x=m=0 and $R_3$=methyl;
alkylpoly(ethylene glycol) (meth)acrylates in which $R_1$ is H or methyl; Z is COO, x=m=0 and $R_3$=alkyl;
phenylpoly(ethylene glycol) (meth)acrylates, also known as poly(ethylene glycol) (meth)acrylate phenyl ether, in which $R_1$ is H or methyl; Z is COO, x=m=0 and $R_3$=phenyl.

Examples of commercial monomers are:
CD 350 (methoxypoly(ethylene glycol 350) methacrylate) and CD 550 (methoxypoly(ethylene glycol 550) methacrylate), supplied by Sartomer Chemicals;
M90G (methoxypoly(ethylene glycol (9 repeating units)) methacrylate) and M230G (methoxypolyethylene glycol (23 repeating units) methacrylate) available from Shin-Nakamura Chemicals;
methoxypoly(ethylene glycol) methacrylates of average molecular weights 300, 475 or 1100, available from Sigma-Aldrich;
methoxypoly(ethylene glycol) acrylate of average molecular weight 426, available from Sigma-Aldrich;
the methoxypoly(ethylene glycol) methacrylates available from Laporte under the trade names: MPEG 350, MPEG 550, S10W and S20W, or from Cognis under the name Bisomer;
poly(ethylene glycol) monomethyl ether, mono(succinimidyl succinate) ester of average molecular weight 1900 or 5000, from Polysciences;
behenyl poly(ethylene glycol PEG-25) methacrylate, available from Rhodia under the name Sipomer BEM;
poly(ethylene glycol) phenyl ether acrylates of average molecular weights 236, 280 or 324, available from Aldrich;
methoxypolyethylene glycol 5000 2-(vinylsulfonyl) ethyl ether commercially available from Fluka;
polyethylene glycol ethyl ether methacrylate available from Aldrich;
polyethylene glycol 8000, 4000, 2000 methacrylates from Monomer & Polymer Dajac Laboratories;
methoxypoly(ethylene glycol) 2000 methacrylate Norsocryl 402 from Arkema;
methoxypoly(ethylene glycol) 5000 methacrylate Norsocryl 405 from Arkema;
poly(ethylene glycol) methyl ether acrylate from Aldrich, Mn=454 g/mol, DP=8-9.

Most particularly, among the monomers with a Tg of less than 20° C., mention may be made of alkyl acrylates in which the alkyl chain comprises from 1 to 10 carbon atoms, with the exception of the tert-butyl group, such as methyl acrylate, isobutyl acrylate and 2-ethylhexyl acrylate; and also poly(ethylene glycol) (meth)acrylates and alkylpoly (ethylene glycol) (meth)acrylates, more particularly methylpoly(ethylene glycol) methacrylates; and mixtures thereof.

The polymer according to the invention may also comprise additional monomers, which may be chosen, alone or as a mixture, from:

- ethylenically unsaturated monomers comprising at least one carboxylic or sulfonic acid function, for instance acrylic acid, methacrylic acid, crotonic acid, maleic anhydride, itaconic acid, fumaric acid, maleic acid, styrenesulfonic acid, acrylamidopropanesulfonic acid, vinylbenzoic acid or vinylphosphoric acid, and salts thereof,
- ethylenically unsaturated monomers comprising at least one hydroxyl function, for instance 2-hydroxypropyl methacrylate, 2-hydroxyethyl methacrylate, 2-hydroxypropyl acrylate or 2-hydroxyethyl acrylate,
- ethylenically unsaturated monomers comprising at least one tertiary amine function, for instance 2-vinylpyridine, 4-vinylpyridine, dimethylaminoethyl methacrylate, diethylaminoethyl methacrylate or dimethylaminopropylmethacrylamide, and salts thereof.

The block with a Tg of greater than or equal to 85° C. preferably comprises at least one acrylate monomer of formula $CH_2=CH-COOR$ and at least one methacrylate monomer of formula $CH_2=C(CH_3)-COOR$ in which R, which may be identical or different, represents a $C_4$ to $C_{12}$ cycloalkyl group and preferably a $C_8$ to $C_{12}$ cycloalkyl; preferably R is identical in the monomers; preferably, these monomers are isobornyl acrylate and methacrylate.

The acrylate monomer and the methacrylate monomer are preferably in mass proportions of between 30/70 and 70/30, preferably between 40/60 and 60/40 and especially of the order of 50/50.

The first block may be obtained exclusively from isobornyl acrylate and methacrylate, which are preferably in an acrylate/methacrylate mass proportion of between 30/70 and 70/30, preferably between 40/60 and 60/40 and especially of the order of 50/50.

The block with a Tg of less than or equal to 20° C. preferably comprises at least one monomer chosen, alone or as a mixture, from

- the acrylates of formula $CH_2=CHCOOR_3$ in which $R_3$ represents a linear or branched $C_1$ to $C_{12}$ unsubstituted alkyl group, with the exception of the tert-butyl group, in which one or more heteroatoms chosen from O, N and S are optionally intercalated; especially isobutyl acrylate,
- the methacrylates of formula $CH_2=C(CH_3)-COOR_4$, in which $R_4$ represents a linear or branched $C_6$ to $C_{12}$ unsubstituted alkyl group, in which one or more heteroatoms chosen from 0, N and S are optionally intercalated,
- (meth)acrylic acid;
- the monomers of formula (I), preferably with x=1 and Z=COO.

Preferentially, the block with a Tg of less than or equal to 20° C. comprises acrylic acid and/or methacrylic acid.

The block ethylenic polymer may be obtained by free-radical solution polymerization according to the following preparation process:

- part of the polymerization solvent may be introduced into a suitable reactor and heated until the adequate temperature for the polymerization is reached (typically between 60 and 120° C.),
- once this temperature has been reached, the constituent monomers of the first block may be added, in the presence of part of the polymerization initiator,
- after a time T corresponding to a maximum degree of conversion of preferably 90%, the constituent monomers of the second block and the rest of the initiator may be introduced,
- the mixture may be left to react for a time T' (ranging especially from 3 to 6 hours) after which the mixture is cooled to ambient temperature (25° C.), so as to obtain the polymer dissolved in the polymerization solvent.

The term "polymerization solvent" is intended to mean a solvent or a mixture of solvents chosen especially from ethyl acetate, butyl acetate, $C_1$-$C_6$ alcohols such as isopropanol or ethanol, and aliphatic alkanes such as isododecane, and mixtures thereof. Preferably, the polymerization solvent is a mixture of butyl acetate and isopropanol or is isododecane.

The polymerization initiator may be chosen from organic peroxides comprising from 8 to 30 carbon atoms. An example that may be mentioned is 2,5-bis(2-ethylhexanoylperoxy)-2,5-dimethylhexane sold under the reference Trigonox® 141 by the company Akzo Nobel.

The block ethylenic polymer according to the invention is preferably prepared by free-radical polymerization and not by controlled or living polymerization. In particular, the polymerization is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

When it is present, the intermediate segment, or intermediate block, which connects the first block and the second block of the block polymer, may result from the polymerization of at least one monomer of the first block, which remains available after the polymerization to a maximum degree of conversion of 90% to form the first block, and of at least one monomer of the second block, added to the reaction mixture. The formation of the second block is initiated when the monomers of the first block no longer react or are no longer incorporated into the polymer chain either because they are all consumed or because their reactivity no longer allows them to be. Thus, the intermediate segment comprises the available monomers of the first block, resulting from a degree of conversion of these first monomers of less than or equal to 90%, during the introduction of the monomers of the second block during the synthesis of the polymer.

Among the block ethylenic polymers of the invention, use will more preferentially be made of a polymer chosen from:

- a poly(isobornyl acrylate/isobornyl methacrylate/isobutyl acrylate/acrylic acid) polymer,
- an isobornyl acrylate/isobornyl methacrylate/PEG methacrylate/acrylic acid random polymer and more particularly a poly(isobornyl acrylate/isobornyl methacrylate/isobutyl acrylate/acrylic acid) polymer.

The block ethylenic polymers according to the invention may be present in the final composition in a content ranging from 0.1% to 10% by weight of active material, preferably in a content ranging from 0.5% to 5% by weight and more preferentially in a content ranging from 0.8% to 3% by weight relative to the total weight of the final composition.

Oily Phase

The antiperspirant composition according to the invention comprises an oily phase, this phase containing i) at least one volatile oil, and ii) at least one nonvolatile hydrocarbon-based oil, and iii) at least one phenyl silicone having a viscosity at 25° C. of less than 1000.0 centistokes.

The term "oil" is intended to mean a fatty substance that is liquid at ambient temperature (25° C.) and atmospheric pressure (760 mmHg, i.e. 105 Pa).

The total amount of oil(s) present in the composition of the invention is preferably in a content ranging from 20% to 90% by weight and more preferentially in a content ranging from 30% to 80% by weight relative to the total weight of the liquid phase (or of the fluid).

For the purposes of the present invention, the term "liquid phase" or "fluid" is intended to mean the base of the composition without the propellant.

Volatile Oils

For the purposes of the invention, the term "volatile oil" is intended to mean an oil that is capable of evaporating on contact with the skin or the keratin fiber in less than one hour, at ambient temperature and atmospheric pressure.

The volatile oils of the invention are volatile cosmetic oils that are liquid at ambient temperature, with a non-zero vapor pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Preferentially, the volatile oil is chosen from hydrocarbon-based volatile oils and silicone volatile oils, or mixtures thereof.

As examples of volatile hydrocarbon-based oils that may be used in the invention, mention may be made of:

volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE10 2008 012 457 from the company Cognis.

As examples of volatile silicone oils that may be used in the invention, mention may be made of:

volatile linear or cyclic silicone oils, especially those with a viscosity ≤8 centistokes ($8 \times 10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;

volatile linear alkyltrisiloxane oils of general formula (I):

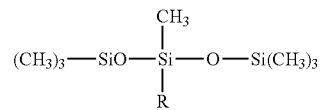

in which R represents an alkyl group comprising from 2 to 4 carbon atoms, one or more hydrogen atoms of which may be replaced with a fluorine or chlorine atom.

Among the oils of general formula (I), mention may be made of:

3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane, corresponding to the oils of formula (I) for which R is, respectively, a butyl group, a propyl group or an ethyl group. The proportion of volatile oil(s) relative to the total amount of oils preferably ranges from 50% to 100% by weight.

Preferably, the volatile oils are chosen from hydrocarbon-based oils and more particularly $C_8$-$C_{16}$ isoalkanes such as isododecane or isohexadecane, or linear $C_8$-$C_{16}$ alkanes such as an undecane/tridecane mixture.

Even more particularly, isododecane will be chosen.

Nonvolatile Hydrocarbon-Based Oils

The term "nonvolatile oil" is intended to mean an oil that remains on the skin or the keratin fiber at ambient temperature and atmospheric pressure for at least several hours, and that especially has a vapor pressure strictly less than $10^{-3}$ mmHg (0.13 Pa).

The term "hydrocarbon-based oil" is intended to mean an oil mainly containing carbon and hydrogen atoms and possibly one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 30 000 mPa·s.

Mention may be made, as examples of nonvolatile oil which can be used in the invention, of:

hydrocarbon-based plant oils such as liquid triglycerides of fatty acids having 4 to 24 carbon atoms, for instance heptanoic or octanoic acid triglycerides, or wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil;

linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms, such as dicaprylyl ether or PPG-14 butyl ether;

synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$-$C_{15}$ alcohol benzoate, hexyl laurate, diisopropyl adipate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols that are liquid at ambient temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

fatty-chain carbonates;

fatty-chain acetates;

fatty-chain citrates;

fluoro oils that are optionally partially hydrocarbon-based and/or silicone-based, for instance fluorosilicone oils, fluoro polyethers and fluorosilicones as described in the document EP-A-847 752.

The oily phase of the compositions according to the invention may contain one or more additional nonvolatile silicone oils other than the phenyl silicones.

As examples of additional nonvolatile silicone oils that may be used in the invention, mention may be made of:

silicone oils, for instance nonvolatile polydimethylsiloxanes (PDMSs); polydimethylsiloxanes comprising alkyl, alkoxy or phenyl groups, which are pendent or at the end of a silicone chain, these groups containing from 2 to 24 carbon atoms; and mixtures thereof.

According to one particular form of the invention, the amount of nonvolatile polydimethylsiloxane(s) will be at most 10% by weight relative to the total weight of the oils.

Preferably, the nonvolatile hydrocarbon-based oils will be chosen from hydrogenated polyisobutene oils such as Parleam®, ethers such as dicaprylyl ether or PPG-14 butyl ether, fatty acid esters such as isopropyl palmitate, isononyl isononanoate or $C_{12}$-$C_{15}$ alkyl benzoates, fatty alcohols such as octyldodecanol, and mixtures thereof.

Fatty acid esters such as isopropyl palmitate, isononyl isononanoate or $C_{12}$-$C_{15}$ alkyl benzoates, and even more particularly isopropyl palmitate, will be chosen more preferentially.

The nonvolatile hydrocarbon-based oil(s) may be present in the liquid phase of the composition in a content ranging from 20% to 90% by weight and preferably in a content ranging from 30% to 80% by weight relative to the total weight of the liquid phase (or of the fluid).

Phenyl Silicone

The composition in accordance with the invention comprises at least one phenyl silicone having a viscosity at 25° C. of less than 1000.0 centistokes (or less than 1000.0 mm²/s).

The term "phenyl silicone" is intended to mean an organopolysiloxane substituted with at least one phenyl group.

The phenyl silicone is preferably nonvolatile. The term "nonvolatile" is intended to mean an oil of which the vapor pressure at ambient temperature and atmospheric pressure is non-zero and is less than 0.02 mmHg (2.66 Pa) and better still less than $10^{-3}$ mmHg (0.13 Pa).

The viscosity at 25° C. of the phenyl silicone in accordance with the invention preferably ranges from 10 to 500 centistokes (i.e. 10 to 500 mm²/s), more particularly from 10 to 50 mm²/s (i.e. 10 to 50 cSt).

The phenyl silicone may be chosen from phenyl trimethicones, phenyl dimethicones, phenyltrimethylsiloxydiphenylsiloxanes, diphenyl dimethicones, diphenyl methyldiphenyl trisiloxanes and 2-phenylethyl trimethylsiloxysilicates. Phenyl trimethicones will more particularly be used.

The phenyl silicone may correspond to the formula:

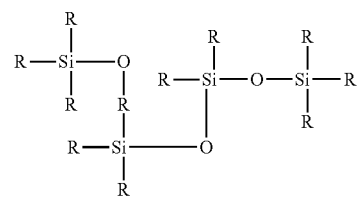

in which the R groups represent, independently of one another, a methyl or a phenyl. Preferably, in this formula, the silicone oil comprises at least three, for example at least four, at least five or at least six, phenyl groups.

According to another embodiment, phenyl silicone corresponds to the formula:

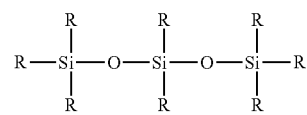

In which the R groups represent, independently of one another, a methyl or a phenyl; said organopolysiloxane comprising at least three phenyl groups, for example at least four or at least five.

Mixtures of the phenyl organopolysiloxanes described above may be used.

Examples that may be mentioned include mixtures of triphenyl, tetraphenyl or pentaphenyl organopolysiloxanes.

According to another embodiment, the phenyl silicone corresponds to the formula:

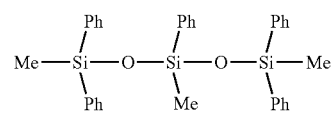

in which Me represents methyl and Ph represents phenyl.

Such a phenyl silicone is especially manufactured by Dow Corning under the reference Dow Corning 555 Cosmetic Fluid (INCI name: trimethyl pentaphenyl trisiloxane). The reference Dow Corning 554 Cosmetic Fluid may also be used.

According to another embodiment, the phenyl silicone corresponds to the formula:

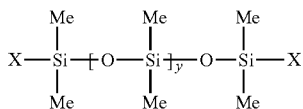

in which Me represents methyl, y is between 1 and 1000 and X represents —CH$_2$—CH(CH$_3$)(Ph).

According to another embodiment, the silicone oil corresponds to the formula:

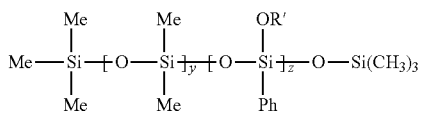

in which —OR' represents —O—SiMe$_3$, y is between 1 and 1000 and z is between 1 and 1000.

The phenyl silicone oil may be chosen from the phenyl silicones of formula (VI) below:

The phenyl silicone oil may be chosen from the phenyl silicones of formula (VII) below:

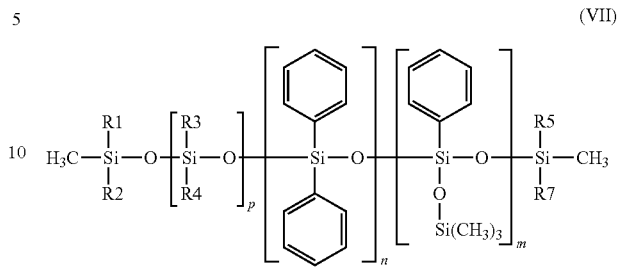

in which:
- R$_1$ to R$_6$, independently of one another, are saturated or unsaturated, linear, cyclic or branched C$_1$-C$_{30}$ hydrocarbon-based radicals,
- m, n and p are, independently of one another, integers between 0 and 100, with the proviso that the sum n+m is between 1 and 100.

Preferably, R$_1$ to R$_6$, independently of one another, represent a saturated, linear or branched C$_1$ to C$_{30}$ and especially C$_1$-C$_{12}$ hydrocarbon-based radical, and in particular a methyl, ethyl, propyl or butyl radical.

R$_1$ to R$_6$ may especially be identical, and in addition may be a methyl radical.

Preferably, m=1 or 2 or 3, and/or n=0 and/or p=0 or 1 may apply, in formula (VII).

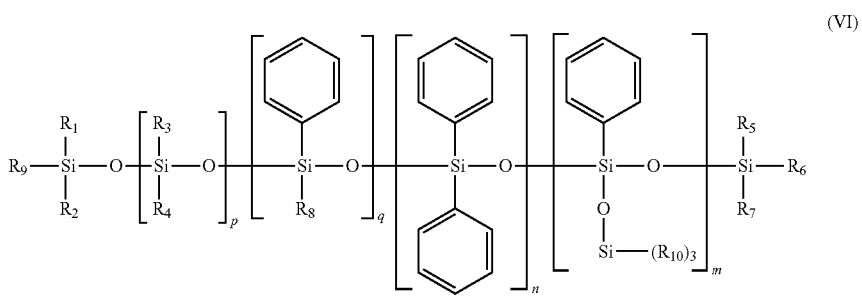

in which

R$_1$ to R$_{10}$, independently of one another, are saturated or unsaturated, linear, cyclic or branched C$_1$-C$_{30}$ hydrocarbon-based radicals, m, n, p and q are, independently of one another, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

As phenyl silicone oil of formula (VII), use may in particular be made of phenyl trimethicones such as Dow Corning 556 Cosmetic Grade Fluid from the company Dow Corning (22.5 cSt), the oil Silbione 70663V30 from Rhône Poulenc (28 cSt), or diphenyl dimethicones such as the Belsil oils, in particular Belsil PDM (1000 cst), Belsil PDM 200 (200 cSt) and Belsil PDM 20 (20 cSt) from Wacker. The values in parentheses represent the viscosities at 25° C.

According to one particularly preferred form of the invention, in order to obtain the least possible transfer of the antiperspirant product onto clothing, use will be made of a phenyl silicone of formula (VII) having a viscosity at 25° C.

ranging from 10 to 500 mm²/s (i.e. 10 to 500 cst), preferably having a viscosity ranging from 10 to 50 mm²/s (i.e. 10 to 100 cSt).

Phenyl trimethicones such as Dow Corning 556 Cosmetic Grade Fluid from the company Dow Corning (22.5 cSt) will even more particularly be used.

The viscosity measurement method used in the invention to characterize the silicone oils according to the invention may be the "kinematic viscosity at 25° C. raw product CID-012-01" or the "Ubbelohde viscosity at 25° C. DIN 51562-1 PV04001".

The proportion of phenyl silicone oil, relative to all the oils, preferably ranges from 0.1% to 20% and more preferentially from 1% to 10% by weight relative to the total weight of the oily phase.

Additives

The cosmetic compositions according to the invention may also comprise cosmetic adjuvants chosen from deodorant active agents, moisture absorbers, lipophilic suspension agents or gelling agents, softeners, antioxidants, opacifiers, stabilizers, moisturizers, vitamins, bactericides, preserving agents, polymers, fragrances, thickeners or suspension agents or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

Deodorant Active Agents

According to a particular form of the invention, the compositions may contain at least one deodorant active agent in the liquid phase.

The term "deodorant active agent" is intended to mean any substance capable of reducing, masking or absorbing human body odors, in particular underarm odors.

The deodorant active agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise); glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), and biguanide derivatives, for instance polyhexamethylene biguanide salts; chlorhexidine and salts thereof; 4-phenyl-4,4-dimethyl-2-butanol (Symdeo MPP® from Symrise); zinc salts such as zinc salicylate, zinc gluconate, zinc pidolate, zinc sulfate, zinc chloride, zinc lactate or zinc phenolsulfonate; salicylic acid and derivatives thereof such as 5-n-octanoylsalicylic acid.

The deodorant active agents may be odor absorbers such as zinc ricinoleates or sodium bicarbonate; metallic or silver or silver-free zeolites, or cyclodextrins and derivatives thereof. They may also be chelating agents such as Dissolvine GL-47-S® from Akzo Nobel, EDTA and DPTA. They may also be a polyol such as glycerol or 1,3-propanediol (Zemea Propanediol sold by Dupont Tate and Lyle BioProducts); or also an enzyme inhibitor such as triethyl citrate; or alum.

The deodorant active agents may also be bactericides or bactericidal agents 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyldodeca-2,5,10-trienol (Farnesol®); quaternary ammonium salts such as cetyltrimethylammonium salts or cetylpyridinium salts.

The deodorant active agents may be present in the composition according to the invention in a proportion from about 0.01% to 20% by weight relative to the total composition, and preferably in a proportion of from about 0.1% to 5% by weight relative to the total weight of the final composition.

Moisture Absorbers

It is also possible to add moisture absorbers, for instance perlites and preferably expanded perlites.

The cosmetic composition may comprise one or more moisture absorbers chosen from perlites.

Preferably, the cosmetic composition comprises one or more absorbers chosen from expanded perlites.

The perlites which can be used according to the invention are generally aluminosilicates of volcanic origin and have the composition:

70.0-75.0% by weight of silica $SiO_2$
12.0-15.0% by weight of aluminum oxide $Al_2O_3$
3.0-5.0% of sodium oxide $Na_2O$
3.0-5.0% of potassium oxide $K_2O$
0.5-2% of iron oxide $Fe_2O_3$
0.2-0.7% of magnesium oxide MgO
0.5-1.5% of calcium oxide CaO
0.05-0.15% of titanium oxide $TiO_2$ The perlite is ground, dried and then calibrated in a first stage. The product obtained, known as perlite ore, is gray-colored and has a size of the order of 100 μm.

The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in patent U.S. Pat. No. 5,002,698.

Preferably, the perlite particles used will be ground; in this case, they are known as Expanded Milled Perlite (EMP). They preferably have a particle size defined by a median diameter D50 ranging from 0.5 to 50 μm and preferably from 0.5 to 40 μm.

Preferably, the perlite particles used have an untamped apparent density at 25° C. ranging from 10 to 400 kg/m³ (standard DIN 53468) and preferably from 10 to 300 kg/m³.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents. The measurements are taken in the same manner by means of the wet point and the flow point, which have, respectively, the following definitions:

wet point: mass expressed in grams per 100 g of product corresponding to the production of a homogeneous paste during the addition of a solvent to a powder;

flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:
Protocol for Measuring the Water Absorption
1) Equipment Used
Glass plate (25×25 mm)
Spatula (wooden shaft and metal part, 15×2.7 mm)
Silk-bristled brush
Balance
2) Procedure The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The average of three tests will be determined.

The expanded perlite particles sold under the trade names Optimat 1430 OR or Optimat 2550 by the company World Minerals will be used in particular.

Suspension Agents/Gelling Agents

The antiperspirant composition according to the invention may also contain one or more suspension agents and/or one or more gelling agents. Some of them may perform both functions simultaneously.

Among the agents that may be used as lipophilic suspension agents and/or gelling agents, mention may be made of clays, in powder form or in oily gel form, said clays possibly being modified, especially modified montmorillonite clays such as hydrophobic-modified bentonites or hectorites, for instance hectorites modified with a $C_{10}$ to $C_{22}$ ammonium chloride, for instance hectorite modified with distearyldimethylammonium chloride, for instance the product disteardimonium hectorite (CTFA name) (product of reaction of hectorite and of distearyldimonium chloride) sold under the name Bentone 38 or Bentone Gel by the company Elementis Specialities. Mention may be made, for example, of the product Stearalkonium Bentonite (CTFA name) (product of reaction of bentonite and of quaternary stearalkonium ammonium chloride) such as the commercial product sold under the name Tixogel MP 250® by the company Sud Chemie Rheologicals, United Catalysts Inc.

Use may also be made of hydrotalcites, in particular hydrophobic-modified hydrotalcites, for instance the products sold under the name Gilugel by the company BK Giulini.

Mention may also be made of fumed silica optionally subjected to a hydrophobic surface treatment, the particle size of which is less than 1 μm. It is in fact possible to chemically modify the surface of the silica, by chemical reaction generating a reduced number of silanol groups present at the surface of the silica. It is possible in particular to replace silanol groups with hydrophobic groups: a hydrophobic silica is then obtained. The hydrophobic groups can be trimethylsiloxyl groups, which are obtained in particular by treatment of fumed silica in the presence of hexamethyldisilazane. Silicas thus treated are named "silica silylate" according to the CTFA (8th edition, 2000). They are sold, for example, under the references Aerosil R812® by the company Degussa, Cab-O-Sil TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are known as Silica dimethyl silylate according to the CTFA (8th Edition, 2000). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

According to a particular form of the invention, the suspension agents or gelling agents may be activated with oils such as propylene carbonate or triethyl citrate.

The amounts of these various constituents that may be present in the composition according to the invention are those conventionally used in compositions for treating perspiration.

Propellant

As indicated previously, the cosmetic composition comprises one or more propellants.

The propellant used in the antiperspirant cosmetic composition according to the invention is chosen from dimethyl ether, volatile hydrocarbons such as propane, isopropane, n-butane, isobutane, n-pentane and isopentane, and mixtures thereof, optionally with at least one chlorohydrocarbon and/or fluorohydrocarbon; among the latter, mention may be made of the compounds sold by the company DuPont de Nemours under the names Freon® and Dymel®, and in particular monofluorotrichloromethane, difluorodichloromethane, tetrafluorodichloroethane and 1,1-difluoroethane sold especially under the trade name Dymel 152 A® by the company DuPont.

Carbon dioxide, nitrous oxide, nitrogen or compressed air may also be used as propellant.

Preferably, the antiperspirant cosmetic composition according to the invention comprises a propellant chosen from volatile hydrocarbons.

More preferentially, the propellant is chosen from isopropane, n-butane, isobutane, pentane and isopentane, and mixtures thereof.

The weight ratio between the liquid phase and the propellant gas varies in a ratio from 5/95 to 50/50, preferably from 10/90 to 40/60 and more preferentially from 15/85 to 30/70.

Preferably, the composition according to the invention comprises:
(i) an oily phase comprising, in a physiologically acceptable medium,
    one or more volatile oils chosen from hydrocarbon-based oils,
    one or more nonvolatile hydrocarbon-based oils, and
        a nonvolatile phenyl silicone oil chosen from phenyltrimethylsiloxanes,
    one or more antiperspirant active agents chosen from aluminum salts,
        one or more water-insoluble film-forming block ethylenic polymers chosen from a poly(isobornyl acrylate/isobornyl methacrylate/isobutyl acrylate/acrylic acid) polymer, an isobornyl acrylate/isobornyl methacrylate/PEG methacrylate/acrylic acid random polymer,
ii) one or more propellants.

The invention also relates to a cosmetic process for treating human perspiration, and optionally the body odors associated with human perspiration, which consists in applying to the surface of the skin an effective amount of the cosmetic composition as described previously.

The application time of the cosmetic composition on the surface of the skin may range from 0.5 to 10 seconds and preferably from 1 to 5 seconds.

The cosmetic composition in accordance with the invention may be applied several times to the surface of the skin.

In particular, the cosmetic treatment process according to the invention consists in applying to the surface of the armpits an effective amount of the cosmetic composition as described above.

The invention also relates to the use of said composition for the cosmetic treatment of human perspiration.

Another subject of the present invention is an aerosol device consisting of a container comprising an aerosol composition as defined previously and of a means for dispensing said composition.

The dispensing means, which forms a part of the aerosol device, generally consists of a dispensing valve controlled by a dispensing head, which itself comprises a nozzle via which the aerosol composition is vaporized. The container containing the pressurized composition may be opaque or transparent. It may be made of glass, of polymer or of metal, optionally coated with a protective varnish coat.

The examples which follow illustrate the present invention without limiting the scope thereof.

Method for Measuring the Transfer

The measurement of the transfer onto clothing was performed according to the protocol described below:

Each of the compositions to be studied was deposited on an imitation leather article sold under the name Supplale® by the company Idemitsu Technofine, which is bonded onto a rigid support. This deposition is performed by spraying the aerosol for 2 seconds at a distance of 15 cm from the support.

After drying for 24 h in an oven at 35° C., a black cotton fabric, which is dry or has been sprayed with artificial* sweat, is deposited on the imitation leather article. A pressure of 1 Newton is applied with a rotational motion on 1 rotation at a speed of 3.14 cm/sec.

The fabric is scanned with a scanner sold under the name Epson V500 Scanner (16-bits gray setting, resolution 300 dpi).

The level of gray of the scans is then analyzed using image software J which has a gray level ranging from 0 to 255. The higher the gray level value, the stronger the marks. It is thus sought to obtain the smallest possible gray level values.

The transfer evaluation is also performed by observation of the residual deposit on the synthetic leather plate:

The persistence is considered as being very good when the deposit is unchanged after the fabric has been passed over.

It is considered as being good when the deposit is visible after the fabric has been passed over.

It is considered as being poor when the deposit is no longer (or only slightly) visible after the fabric has been passed over.

*Composition of the artificial sweat:

| Ingredients | % by weight |
| --- | --- |
| NaCl | 0.5% (85.6 mM) |
| lactic acid | 0.1% (11.1 mM) |
| Urea | 0.1% (14.7 mM) |
| Albumin | 0.10% |
| $NH_4OH$ | qs pH 6.5 |

Tackiness Test:

The tackiness was measured according to the protocol described below:

3.75 $mg/cm^2$ of product are spread on a specific support constituted of a poly(methyl methacrylate) (PMMA) plate to which the Supplale support from Idemitsu is attached. After uniform spreading of the product, the plate with the film is placed under the texture analyzer equipped with a cylindrical probe which is 18 mm in diameter, to which an 18 mm disk of Bioskin support (Bioskin plate black K275 from Maprecos SAS) has been attached—and has been covered with a Supplale support.

The texture analyzer is placed in a glovebox so as to work in a temperature- and humidity-controlled atmosphere.

The probe comes to apply a force of 400 g on the sample.

The apparatus then calculates the force required for the probe to separate from the sample. In the case of the experiment, only the maximum force which represents the strength of the tackiness of the formula at this given moment is retained. This type of measurement is carried out every 30 seconds for 320 seconds.

The evaluation of the tackiness is the following:

The tackiness is considered to be low when the detachment force is less than 60 g.

The tackiness is considered to be medium when the detachment force is between 60 g and 120 g.

The tackiness is considered to be high when the detachment force is greater than 120 g.

EXAMPLE 1

The formulae tested in aerosol form comprise a base manufactured according to the process described below and containing the ingredients mentioned in the following table:

| Phase | Ingredients | Fluid Example 1 (invention) | Fluid Comparative example C1 | Fluid Comparative example C2 |
| --- | --- | --- | --- | --- |
| A | Isopropyl palmitate[1] | 9.15 | 12.29 | 9.15 |
|  | Isododecane[2] | 32 | 32 | 32 |
|  | Acrylic acid/isobutyl acrylate/isobornyl acrylate copolymer (50% in isododecane)[3] | 16 | 16 | 16 |
|  | Phenyl Trimethicone[4] 22.5 cSt | 3.14 | 0 | — |
|  | Diphenyl Dimethicone[5] 1000 cSt | — | 0 | 3.14 |
| B | Disteardimonium hectorite[6] | 2.6 | 2.6 | 2.6 |
| C | Propylene carbonate[7] | 0.78 | 0.78 | 0.78 |
| D | Aluminum chlorohydrate[8] | 35 | 35 | 35 |
|  | Perlite[9] | 1.33 | 1.33 | 1.33 |

[1] sold under the trade name Isopropyl Palmitate by the company Cognis (BASF)
[2] sold under the trade name Isododecane by the company Ineos
[3] sold under the trade name Mexomere PAS by the company Chimex
[4] sold under the trade name Dow Corning Cosmetic Grade Fluid by the company Dow Corning
[5] sold under the trade name Belsil PDM1000 by the company Wacker
[6] sold under the trade name Bentone 38VCG by the company Elementis
[7] sold under the trade name Jeffsol propylene carbonate by the company Huntsman
[8] sold under the trade name Reach 103 by the company Summitreheis
[9] sold under the trade name Optimat 2550 OR by the company Worldminerals (Imerys)

Phase A was mixed with stirring. Phase (B) was introduced slowly into phase (A) and the mixture was then left to swell for five minutes. (C) was introduced. The mixture was stirred vigorously until good homogenization was obtained.

The aluminum chlorohydrate and the perlite (D) were then added portionwise. Stirring was continued to obtain good homogenization.

The bases thus formulated were packaged in cans and a propellant was added to the above preparations according to the following schemes:

| Aerosol | Example 1 | Comparative example C1 | Comparative example C2 |
|---|---|---|---|
| Fluid Example 1 | 15 | — | — |
| Fluid Comparative Example C1 | — | 15 | — |
| Fluid Comparative Example C2 | — | — | 15 |
| Isobutane | 85 | 85 | 85 |

Results Regarding Transfer-Resistance Efficacy and Regarding Tackiness

The example 1 aerosol with a phenyl silicone having a viscosity at 25° C. of 22.5 cSt was sprayed under the conditions described above and the results obtained in comparison with the aerosol without phenyl silicone (comparative C1) and with a phenyl silicone having a viscosity at 25° C. of 1000 cSt (comparative C2) are described in the table below:

| Aerosol | Example 1 with Phenyl Trimethicone (invention) having a viscosity at 25° C. of 22.5 cSt | Comparative Example C1 without Phenyl Trimethicone | Example 2 with Diphenyl Trimethicone (invention) having a viscosity at 25° C. of 1000 cSt |
|---|---|---|---|
| Level of gray dry | 48.52 ± 1.17 | 50.51 ± 1.54 | 50.29 ± 1.07 |
| Level of gray with the artificial sweat | 42.40 ± 0.36 | 48.33 ± 8.62 | 51.01 ± 1.67 |
| Tackiness | 40 low | 150 high | 100 medium |

It was noted that, in the case of the composition of example 1, the persistence was lower when dry and with the artificial sweat than that of composition C1 and than that of the composition of example 2.

It was noted that the tacky effect was substantially decreased with examples 1 and 2 of the invention comprising a phenyl silicone compared with the very high tackiness of composition C1 not containing phenyl silicone.

EXAMPLE 2

The formulae tested in aerosol form comprise a base manufactured according to the process described below and containing the ingredients mentioned in the following table:

| Phase | Ingredients | Preparation Invention Example 2 | Comparative Preparation C3 |
|---|---|---|---|
| A | Isopropyl palmitate[1] | 0.86 | 3.215 |
| A | Isododecane[2] | 24 | 24 |
| A | Cocos nucifera (coconut) oil[3] | 0.315 | 0.315 |
| A | Acrylic acid/isobutyl acrylate/isobornyl acrylate copolymer (50% in isododecane)[4] | 12 | 12 |
| A | Phenyl trimethicone[5] | 2.355 | 0 |
| B | Disteardimonium hectorite[6] | 2.6 | 2.6 |
| C | Propylene carbonate[7] | 0.87 | 0.87 |
| D | Aluminum chlorohydrate[8] | 35 | 35 |
| D | Aluminum sesquichlorohydrate[9] | 15 | 15 |
| | Fragrance | 7 | 7 |

[1] sold under the trade name Isopropyl Palmitate by the company Cognis (BASF)
[2] sold under the trade name Isododecane by the company Ineos
[3] sold under the trade name refined coconut oil GV 24/26 by the company Sio (ADM)
[4] sold under the trade name Mexomere PAS by the company Chimex
[5] sold under the trade name Dow Corning Cosmetic Grade Fluid by the company Dow Corning
[6] sold under the trade name Bentone 38VCG by the company Elementis
[7] sold under the trade name Jeffsol propylene carbonate by the company Huntsman
[8] sold under the trade name Reach 103 by the company Summitreheis
[9] sold under the trade name Reach 301 by the company Summitreheis Phase A was mixed with stirring. Phase (B) was introduced slowly into phase (A) and the mixture was then left to swell for five minutes. (C) was introduced. The mixture was stirred vigorously until good homogenization was obtained. The aluminum chlorohydrate and the aluminum sesquichlorohydrate (D) were then added portionwise. Stirring was continued to obtain good homogenization. The fragrance was added. The bases thus formulated were packaged in cans and a propellant was added to the above preparations according to the following schemes:

| Aerosol | Example 2 (Invention) | Comparative C3 |
|---|---|---|
| Preparation Ex 2 | 20 | — |
| Preparation C3 | — | 20 |
| Isobutane | 80 | 80 |

The example 2 aerosol with phenyl trimethicone, having a viscosity at 25° C. of 22.5 cSt, was sprayed under the conditions described above and the results obtained in comparison with the aerosol without phenyl trimethicone (comparative C3) are described in the table below:

| Aerosol | Example 2 with Phenyl Trimethicone 22.5 cSt (invention) | Comparative Example C3 without Phenyl Trimethicone (outside the invention) |
|---|---|---|
| Level of gray dry | 47.2 ± 1.1 | 57.9 ± 0.9 |
| Level of gray with the artificial sweat | 45.80 ± 1.6 | 49.4 ± 1.5 |
| Tackiness | 40 low | 120 high |

It was noted that, in the case of the composition of example 2 with phenyl silicone, the transfer was lower than in the case of composition C3 without phenyl silicone.

It was noted that, in the case of the composition of example 2, the tackiness is judged to be low, while in the case of composition C3, the tackiness is judged to be very high.

The invention claimed is:

1. An anhydrous composition in aerosol form comprising 1) a fluid phase that comprises a), b) and c) wherein:
   a) is an oily phase in an amount ranging from 20% to 90% by weight of the fluid phase and comprising
      i) at least one hydrocarbon-based oil volatile oil,
      ii) at least one nonvolatile hydrocarbon-based oil, and
      iii) at least one phenyl silicone having a viscosity at 25° C. of less than 1000.0 mm²/s, and
   b) is at least one antiperspirant active agent chosen from aluminum and/or zirconium salts or complexes in an amount ranging from 1% to 25% by weight of the anhydrous composition, and
   c) at least one water-insoluble non-elastomeric film-forming block ethylenic polymer in an amount ranging from 0.1% to 10% by weight of the anhydrous composition, wherein said at least one water-insoluble non-elastomeric film-forming block ethylenic polymer comprises a first block with a glass transition temperature (Tg) of greater than or equal to 85° C. and a second block with a Tg of less than or equal to 20° C., and in that said first and second blocks are linked together via an intermediate segment comprising at least one constituent monomer of said first block and at least one constituent monomer of said second block, and
   2) at least one propellant; and
   wherein the weight ratio of the fluid phase and the at least one propellant is from 5/95 to 50/50.

2. The composition as claimed in claim 1, wherein the aluminum and/or zirconium salts or complexes are chosen from aluminum chlorohydrate, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the aluminum sesquichlorohydrex-propylene glycol complex, aluminum sulfate buffered with sodium aluminum lactate, aluminum zirconium octachlorohydrate, aluminum zirconium pentachlorohydrate, aluminum zirconium tetrachlorohydrate, aluminum zirconium trichlorohydrate, and the aluminum zirconium octachlorohydrex-glycine, aluminum zirconium pentachlorohydrex-glycine, aluminum zirconium tetrachlorohydrex-glycine and aluminum zirconium trichlorohydrex-glycine complexes.

3. The composition as claimed in claim 2 wherein the antiperspirant active agent is aluminum chlorohydrate and/or aluminum sesquichlorohydrate.

4. The composition as claimed in claim 1, wherein the block with a Tg of greater than or equal to 85° C. comprises at least one monomer with a Tg of greater than or equal to 85° C., chosen from the following monomers, alone or as a mixture:
   the methacrylates of formula $CH_2\!=\!C(CH_3)\!-\!COOR_1$ in which $R_1$ represents a methyl or tert-butyl group; or a $C_6$ to $C_{12}$ cycloalkyl group;
   the acrylates of formula $CH_2\!=\!CH\!-\!COOR_2$ in which $R_2$ represents a $C_6$ to $C_{12}$ cycloalkyl group or a tert-butyl group;
   the (meth)acrylamides of formula $CH_2\!=\!C(CH_3)\!-\!CONR_7R_8$ or $CH_2\!=\!CH\!-\!CONR_7R_8$, in which $R_7$ and $R_8$, which may be identical or different, represent a hydrogen atom or a methyl or isopropyl group; or $R_7$ represents H and $R_8$ represents a branched $C_3$ to $C_5$ group;
   styrene and derivatives thereof.

5. The composition as claimed claim 1, wherein the block with a Tg of greater than or equal to 85° C. comprises at least one monomer with a Tg of greater than or equal to 85° C., chosen from methyl methacrylate, tert-butyl (meth)acrylate and isobornyl (meth)acrylate, and mixtures thereof.

6. The composition as claimed in claim 1, wherein the block with a Tg of less than or equal to 20° C. comprises at least one monomer with a Tg of less than or equal to 20° C., chosen from the following monomers, alone or as a mixture:
   the acrylates of formula $CH_2\!=\!CHCOOR_3$, with $R_3$ representing a linear or branched $C_1$ to $C_{12}$ alkyl group, with the exception of the tert-butyl group, in which one or more heteroatoms chosen from O, N and S are optionally intercalated, said alkyl group also optionally being substituted with one or more substituents chosen from hydroxyl groups and halogen atoms;
   the methacrylates of formula $CH_2\!=\!C(CH_3)\!-\!COOR_4$, with $R_4$ representing a linear or branched $C_6$ to $C_{12}$ alkyl group, in which one or more heteroatoms chosen from O, N and S are optionally intercalated, said alkyl group also optionally being substituted with one or more substituents chosen from hydroxyl groups and halogen atoms;
   the vinyl esters of formula $R_5\!-\!co\!-\!O\!-\!CH\!=\!CH_2$ in which $R_5$ represents a linear or branched $C_4$ to $C_{12}$ alkyl group;
   $C_4$ to $C_{12}$ alkyl vinyl ethers;
   $N\!-\!(C_4$ to $C_{12})$alkyl acrylamides;
   the monomers of formula (I) below, alone or as a mixture:

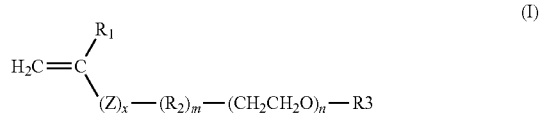

(I)

in which:
   $R_1$ is a hydrogen atom or a methyl radical;
   Z is a divalent group chosen from —COO—, —CONH—, —CONCH$_3$,—CO—O—, —O—, —SO$_2$— —CO—O—CO— and —CO—CH$_2$—CO—;
   x is 0 or 1;
   $R_2$ is a linear, branched or cyclic, saturated or unsaturated, optionally aromatic divalent carbon-based radical, of 1 to 30 carbon atoms, which may comprise 1 to 18 heteroatoms chosen from O, N, S, F, Si and P;
   m is 0 or 1;
   n is an integer between 3 and 300 inclusive;
   $R_3$ is a hydrogen atom or a linear, branched or cyclic, saturated or unsaturated, optionally aromatic carbon-based radical, of 1 to 30 carbon atoms, which optionally comprises 1 to 20 heteroatoms chosen from O, N, S, F, Si and P.

7. The composition as claimed in claim 1, wherein the block with a Tg of less than or equal to 20° C. comprises at least one monomer with a Tg of less than or equal to 20° C., chosen from alkyl acrylates in which the alkyl chain comprises from 1 to 10 carbon atoms, with the exception of the tert-butyl group; and poly(ethylene glycol) (meth)acrylates and alkylpoly(ethylene glycol) (meth)acrylates; and mixtures thereof.

8. The composition as claimed in claim 1, wherein the water-insoluble non-elastomeric film-forming block ethylenic polymer is chosen from:
   a poly(isobornyl acrylate/isobornyl methacrylate/isobutyl acrylate/acrylic acid) polymer,
   an isobornyl acrylate/isobornyl methacrylate/PEG methacrylate/acrylic acid random polymer.

9. The composition as claimed in claim 1, wherein the propellant is chosen from dimethyl ether, volatile hydrocarbons such as n-butane, propane, isopropane, isobutane, pentane and isopentane, and mixtures thereof, optionally with at least one chlorohydrocarbon and/or fluorohydrocarbon.

10. The composition as claimed in claim 1, wherein the weight ratio between the liquid phase and the propellant gas varies in a ratio from 10/90 to 40/60.

11. The composition as claimed in claim 1, wherein the volatile oil is chosen from $C_8$-$C_{16}$ volatile hydrocarbon-based oils.

12. The composition as claimed in claim 1, wherein the nonvolatile hydrocarbon-based oil(s) is (are) chosen from hydrogenated polyisobutene oils, ethers, fatty acid esters, fatty alcohols and mixtures thereof.

13. The composition as claimed claim 1, wherein the proportion of phenyl silicone, relative to all the oils ranges from 0.1% to 20% by weight.

14. The composition as claimed in claim 1, wherein the nonvolatile phenyl silicone is chosen from the phenyl silicones of formula (VII) below:

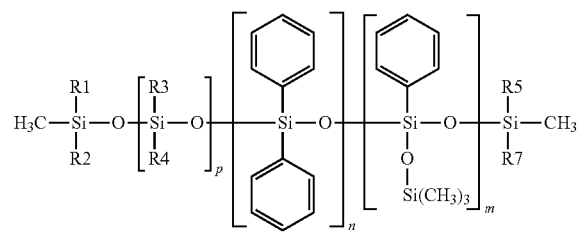

(VII)

in which:
   $R_1$ to $R_6$, independently of one another, are saturated or unsaturated, linear, cyclic or branched $C_1$-$C_{30}$ hydrocarbon-based radicals,
   m, n and p are, independently of one another, integers between 0 and 100, with the proviso that the sum n+m is between 1 and 100.

15. The composition as claimed in claim 14, wherein the viscosity at 25° C. of the phenyl silicone is from 10 to 500 mm²/s.

16. The composition as claimed in claim 1, wherein the phenyl silicone is chosen from phenyl trimethicones.

17. The composition as claimed in claim 1, which also comprises one or more moisture absorbers chosen from perlites.

18. A cosmetic process for treating human perspiration, and optionally the body odors associated with human perspiration, which comprises applying to the surface of the skin an effective amount of the composition as defined in claim 1.

19. An aerosol device consisting of a container comprising an aerosol composition as defined according to claim 1 and of a means for dispensing said aerosol composition.

20. The composition as claimed in claim 1, wherein the water-insoluble non-elastomeric film-forming block ethylenic polymer is a poly(isobornyl acrylate/isobornyl methacrylate/isobutyl acrylate/acrylic acid) polymer.

21. The composition as claimed in claim 1, being free from silicone volatile oils.

22. The composition as claimed in claim 1, wherein the viscosity at 25° C. of the phenyl silicone is from 10 to 500 mm²/s.

23. The composition as claimed in claim 1, wherein the phenyl silicone is chosen from phenyl trimethicones, phenyl dimethicones, phenyltrimethylsiloxydiphenylsiloxanes, diphenyl dimethicones, diphenyl methyldiphenyl trisiloxanes and 2-phenylethyl trimethylsiloxysilicates.

* * * * *